United States Patent [19]

Spence et al.

[11] 4,362,633

[45] Dec. 7, 1982

[54] MOLYBDENUM-CONTAINING AMINATED SULFURIZED OLEFIN LUBRICATING OIL ADDITIVES

[75] Inventors: J. Ronald Spence, Bartlesville, Okla.; C. Thomas West, Naperville, Ill.

[73] Assignee: Standard Oil Company (Indiana), Chicago, Ill.

[21] Appl. No.: 196,055

[22] Filed: Oct. 10, 1980

[51] Int. Cl.$^3$ .............................................. C10M 1/54
[52] U.S. Cl. .................................. 252/46.4; 252/49.7; 260/125; 260/132
[58] Field of Search ................... 252/46.4, 49.7, 46.7; 260/132, 125

[56] References Cited

U.S. PATENT DOCUMENTS

| | | | |
|---|---|---|---|
| 2,316,084 | 4/1943 | Loane et al. | 252/46.4 X |
| 2,987,478 | 6/1961 | Matson | 252/46.4 |
| 3,290,245 | 12/1966 | Elliott et al. | 252/49.7 X |
| 3,574,576 | 4/1971 | Honnen et al. | 252/32.7 E X |
| 4,119,549 | 10/1978 | Davis | 252/46.4 X |
| 4,259,194 | 3/1981 | deVries et al. | 252/34.7 X |
| 4,259,195 | 3/1981 | King et al. | 252/34.7 X |
| 4,261,843 | 4/1981 | King et al. | 252/34.7 X |
| 4,263,152 | 4/1981 | King et al. | 252/34.7 X |
| 4,272,387 | 6/1981 | King et al. | 252/46.4 |
| 4,283,295 | 8/1981 | deVries et al. | 252/34.7 X |
| 4,285,822 | 8/1981 | deVries et al. | 252/34.7 X |

*Primary Examiner*—Andrew Metz
*Attorney, Agent, or Firm*—Richard A. Kretchmer; William T. McClain; William H. Magidson

[57] ABSTRACT

The reaction product of an olefin, sulfur or sulfur-yielding compound, an amine and a molybdenum compound is a highly effective lubricant additive providing friction modification, antioxidant activity and dispersancy.

11 Claims, No Drawings

MOLYBDENUM-CONTAINING AMINATED SULFURIZED OLEFIN LUBRICATING OIL ADDITIVES

This invention relates to novel molybdenum-containing compositions which provide a variety of beneficial properties to lubricating oils used in internal combustion engines. More particularly, this invention relates to novel molybdenum-containing compositions which provide friction modification, antioxidant activity, and dispersancy to lubricating oils, and to novel methods of preparation of the molybdenum compositions.

Lubricating oil additives that provide beneficial properties to the lubricating oil include dispersants that are capable of limiting formation of deposits in internal combustion engines by suspending in the oil, insoluble combustion products of gasoline and lubricating oils; antioxidant additives that prevent the oxidation and thickening of lubricating oils extending the effective life of the lubricant; and friction modifiers that improve engine efficiency by reducing friction between moving parts in the engine. Important advantages are realized by combining these properties in a single additive composition. Lesser amounts of the additive are required to provide protection to the engine, and harmful haze and precipitate forming interactions between different additive compositions can be avoided. While a variety of additive compositiations are available for commercial use in lubricating oils, many of these compounds fail to combine friction modification, anti-oxidation and dispersancy properties in a single composition.

A variety of organic molybdenum-containing compounds and processes for the solubilization of molybdenum compounds have been disclosed in recent years. These processes tend to be undesirable since the products often have limited solubility in lubricating oils, are inefficient in solubilizing molybdenum, require the use of expensive materials or expensive procedures, and produce additives which have minimal dispersancy, antiwear or friction modifying activity.

Accordingly, a need exists for a molybdenum-containing additive which provides low cost friction modification, antioxidant activity (oxidation resistance), and dispersancy to lubricating oils.

The general object of this invention is to improve the properties of lubricating oil with molybdenum-containing compositions. Another object of the invention is to provide a lubricating oil additive that combines friction modification, oxidation resistance, and dispersancy. Another object of the invention is to provide a novel process for the efficient solubilization of molybdenum compounds producing effective molybdenum-containing lubricating oil compositions. Further objects appear hereinafter.

We have discovered a novel composition comprising the reaction product of an olefin, sulfur or sulfur-yielding compound, an amine, and a molybdenum compound that provides friction modification, oxidation resistance, and dispersancy at reasonable cost to lubricating oils. We have found that these molybdenum-containing sulfurized aminated olefins provide through the combination of these components unexpected and highly effective properties.

Briefly, the novel additives of this invention are prepared by the reaction of an olefin, a sulfur or sulfur-yielding compound, an amine, and a molybdenum compound.

Molybdenum compounds useful in preparing the novel lubricating oil additives of this invention are those which produce ammonium molybdate, molybdic acid, including iso- and heteropoly molybdic acid, molybdic oxides or sulfides under reaction conditions. Such compounds include ammonium molybdate, molybdenum oxides and sulfides, and a Group I metal, Group II metal or ammonium salt of molybdic acid including sodium molybdate, potassium molybdate, magnesium molybdate, calcium molybdate, barium molybdate, ammonium molybdate, a molydenum-halide, etc. Preferably molybdenum trioxide ($MoO_3$, molybdic anhydride) for reasons of reactivity, low cost, and availability can be used. Other compounds of molybdenum such as molybdenum halide, molybdenum dioxide, molybdenum sesquioxide, ammonium thiomolybdate, ammonium bismolybdate, ammonium heptamolybdate tetrahydrate, etc. can also be employed. Other molybdenum compounds which can be useful in this invention are discussed in U.S. Pat. Nos. 2,753,306; 2,758,089; 3,140,997; and 3,256,184, which are expressly incorporated by reference herein.

The olefin constituent useful in the preparation of the novel additives of this invention comprises mono- or polyunsaturated hydrocarbons including olefins recovered from refinery streams, polyolefins, etc. having 10 to 10,000 carbon atoms. These olefins include decene, t-decene, t-dodecene, 2-decene, iso-octadecene, etc. The atactic or amorphous polymers produced by the polymerization of low molecular weight olefin can also be used. The manufacture of the polyolefins can be obtained by contacting an olefin or a mixture of olefins generally in liquid phase with catalyst such as sulfuric acid, boron trifluoride, aluminum chloride, Ziegler-Natta or other similar catalysts well known in the art. Preferably, olefinic polymers can be derived from $C_{2-18}$ olefins or $C_{4-15}$ conjugated or $C_{5-15}$ nonconjugated dienes including ethylene (ethene), propylene (propene), 1-butene, 2-butene, isobutylene (2-methyl-propene), or conjugated or nonconjugated dienes such as butadiene, norbornadiene, 5-methylene-norbornene, 5-ethylidene norbornene, etc. The preferred substantially amorphous or viscous polyolefin comprises an ethylene-propylene copolymer, an ethylene-propylene-diene terpolymer, an ethylene-propylene-norbornene polymer including ethylene-propylene-5-ethylidene-2-norbornene terpolymer, polyisobutylene, etc., or mixtures thereof having a molecular weight from about 150 to about 200,000 or greater. Preferably, polymers having a molecular weight from about 300 to about 50,000 are used for reasons of economy and reactivity.

Amines useful in preparing the novel lubricating oil additives of this invention include aliphatic amines and polyamines having the general formula $NH_2(CH_2)_yNH_2$, wherein y is an integer of 2 to 12; polyalkylenepolyamines of the general formula $NH_2[(CH_2)_z-NH]_xH$, wherein z is an integer from 2 to 6 and x is an integer from 1 to 10. Illustrative of suitable amines are methylamine, butylamine, cyclohexylamine, propylamine, decylamine, ethylenediamine, trimethylenediamine, tetramethylenediamine, hexamethylenediamine, diethylenetriamine, triethylenetetramine, tetraethylenepentamine, tripropylenetetramine, tetrapropylenepentamine, hexamethylene diamine and mixtures thereof and other polyalkylene-polyamines in which the alkylene group contains up to about 12 carbon atoms. Other useful polyamines include a N-(aminoalkyl)-morpholine, a 1,3-propane polyamine, a polyoxy polyamine, a bis(aminoalkyl)piperazine a bis-(aminoalkyl)ethylenediamine, and a bis(aminoalkyl)-propylenediamine.

Sulfur can be used to produce the lubricating oil additives of this invention in a solid or molten form of elemental sulfur or as a sulfur-yielding compound such as sulfur monochloride or sulfur dichloride. Other sulfur-yielding compounds include hydrogen sulfide, phosphorus pentasulfide, etc. Fine particulate or molten elemental sulfur is preferred for reasons of ease of handling, availability and low cost.

In somewhat greater detail, the novel products of this invention can be produced by reacting an olefin, sulfur or a sulfur-yielding compound, an amine and a molybdenum compound. However, to afford reaction control and improved product, the following reaction sequence is preferred: (A) reacting the olefin and sulfur to produce a sulfurized olefin; (B) reacting the sulfurized olefin with an amine to produce an aminated sulfurized olefin; and (C) reacting the aminated sulfurized olefin with a molybdenum compound to produce the finished additive.

About 0.1-20 moles of sulfur or sulfur-yielding material can be reacted with the olefin per mole of olefin compound to form the sulfur-yielding compound. Preferably, from about 0.5-10 moles of sulfur are reacted with the olefin per mole of olefin compound to provide essentially optimal sulfurization.

The temperature range of the sulfurization reaction is generally about 50°-500° C. preferably about 100°-250° C. The most preferred temperature range is between about 150°-200° C. for reasons of rapid reaction rate and reduced decomposition of reactants. Frequently, sulfurization catalysts are added to the reaction mixture to increase the yield or rate of the reaction. These mixtures include acidified clays, paratoluene sulfonic acid, dialkylphosphorodithioic acid, and a phosphorus sulfide.

The time required to complete the sulfurization will vary depending on the ratios of reactants, reaction temperature, catalysts used, and purity of reagents. The course of the reaction is conveniently monitored by following reaction vessel pressure or evolution of hydrogen sulfide. The reaction can be considered complete when the pressure levels off or the evolutin of hydrogen sulfide subsides. Following the sulfurization reaction, substantially all volatile materials can be removed. If desired volatile materials can be removed by stripping the sulfurized olefin with an inert gas at an elevated temperature for a period of time so that substantially all volatile materials have been removed.

The olefin or polyolefin can be either mechanically or oxidatively degraded prior to reaction with sulfur or amine. Mechanical degradation is commonly performed in well-known processes in apparatus, such as blenders or homogenizers, directing high shear forces on the polymer solution. The mechanical degradation reduces viscosity and molecular weight to the desired level. Oxidative degradation is commonly performed by contacting the olefin or polyolefin in solution with oxidizing agents such as an oxygen-containing gas to introduce carbonyl, aldehyde, alcohol and other oxygen-containing groups into the polymer chain. The oxygen-containing groups produce active sites on adjacent carbon atoms that participate in a variety of reactions useful for production of derivatives of the polymer. Further details of oxidation of olefins or polyolefins is disclosed in Ser. No. 196,051 filed Oct. 10, 1980 which is copending with this application, and which is expressly incorporated by reference herein.

The sulfurized olefin can be reacted with from about 0.1-20 moles of amine per mole of olefin. Commonly, about 0.5-20 moles of amine per mole of sulfurized olefin are used for reasons of high dispersancy and low cost of the resulting product. The amination reaction is commonly performed at a temperature between about 50°-400° C., preferably at a temperature of about 150°-200° C. for reasons of rapid reaction and low degradation of products. While the reaction time is variable depending on purity and concentration and ratio of reactants, the reaction commonly is complete in about 2 to 24 hours. Volatile and particulate materials can be conveniently removed at this point.

In order to reduce side reactions and to improve filterability of the aminated sulfurized olefin, the amination reaction can be run in the presence of about 0.1 to about 10 moles of a metal oxide or hydroxide per mole of olefin. Either amination or sulfurization, or both, can produce great quantities of tarry by-products which can prevent filtration and other purification steps. The metal oxide or hydroxide reduces tar formation and adsorbs the tar rendering the tarry material less sticky and the reaction mixture filterable. Preferably alkali metal or alkaline earth metal compounds such as lithium hydroxide, sodium hydroxide, potassium chloride, calcium oxide, barium oxide, calcium hydroxide, calcium chloride, magnesium oxide, magnesium hydroxide, or magnesium sulfate, can be added to the reaction mixture. The tarry-metal compound reaction product then precipitates and can be easily removed by washing or filtration. Commonly, the metal compound can be added simultaneously with the amine, prior to the amine or after the amine. However, the best results are obtained when the alkaline earth metal is added prior to or simultaneously with the amine.

The aminated sulfurized olefin can be reacted with a molybdenum compound. Molybdenum compounds can be added solid or in organic or aqueous solution or suspension. Preferably the molybdenum compound is solubilized or suspended in an aqueous solution and contacted with the aminated sulfurized olefin. About 0.1-10 moles of molybdenum compound can be combined per mole of olefin. Preferably, about equimolar amounts of molybdenum compound and sulfurized aminated olefin are used for reasons of rapid reaction, high friction reduction of product, and low consumption of molybdenum. The reaction can run at temperatures from 50° C. to about 300° C.; however, the reaction is preferably run at reflux and at atmospheric pressure. Depending on reactant purity, reactant ratios, and temperature, the reaction commonly is complete in about 2 to 24 hours. At the end of the reaction, water and other volatile constituents can be stripped by heating and passing an inert gas through the reaction mixture. Commonly, the mixture can be filtered through celite to remove undesirable precipitate.

The reactions detailed above can be performed in batch or continuous mode. In batch mode the reactant or reactants in appropriate diluent are added to a suitable vessel for reaction. The product is then withdrawn to appropriate strippers, filters and other purification apparatus. In continuous mode a stream of reactant or reactants is continuously combined at an appropriate rate and ratio in a vertical or horizontal reaction zone maintained at the reaction temperature. The reaction mixture stream is continuously withdrawn from the zone and is directed to appropriate strippers, filters and purification apparatus.

The reactions can be run neat (solventless) or in inert solvents or diluents such as hexane, heptane, benzene, toluene, lubricating oil, petroleum fractions, kerosene, lingroin, petroleum ether, etc., under an inert gas blanket such as nitrogen, argon, etc.

The reaction can be run at atmospheric or superatmospheric pressure maintained by gases evolved during reaction or by inert pressurizing gases.

The above described reaction products of the present invention are effective additives for lubricating oil compositions when used in amounts of from about 0.1–90 weight percent based on the oil. Suitable lubricating base oils are mineral oils, petroleum oils, synthetic lubricating oils such as those obtained by polymerization of hydrocarbons and other well known synthetic lubricating oils, and lubricating oils of animal or vegetable origin. Concentrates of the additive composition of the invention in a suitable base oil containing about 10 to 90 weight percent of the additive based on the oil alone or in combination with other well known additives can be used for blending with the lubricating oil in proportions designed to produce finished lubricants containing 0.1 to 10 wt% of the product.

The additives of this invention are often evaluated for dispersancy, varnish inhibiting property (oxidation resistance) and friction modification using the Spot Dispersancy Test, the Hot Tube Test, the Amihot Test, and the Motored Engine Test.

In the Spot Dispersancy Test (SDT), the ability of the additive in the lubricating oils to suspend and disperse engine sludge was tested. To perform this test, an amount of engine sludge produced in a VC or VD engine test is mixed with an amount (4.0–15.0 wt.% based on the sludge) of the test additive. The sludge and additive are incubated in an oven at 146° C. for 24 hours. After this period, the mixture is spotted on a clean white blotter paper. The oil diffuses through the blotter paper carrying the sludge to some extent, depending on the dispersancy of the additive, forming an oil diffusion ring and a sludge diffusion ring. The dispersancy of the additive is computed by dividing the diameter of the sludge ring by the diameter of the oil ring, multiplying the result by 100 percent dispersancy. The higher the number, the better dispersant property of the additive.

In the Hot Tube Test (HTT) the high temperature, varnish inhibiting properties of the additive are determined. A measured portion of a lubricating oil containing the additive in question is slowly metered into a 2 millimeter glass tube heated in an aluminum block. Through the tube is passed either nitrogen oxides or air at 201.7° C. (395° F.) or 257.2° C. (495° F.). During the test, the oil is consumed, and the ability of the additive to prevent the formation of varnish deposits is measured by the ability of the additive to prevent the formation of colored deposits on the interior surface of the tube. The tube is rated from 10 to 1 wherein 10 is perfectly clean and colorless and 1 is opaque and black.

In the Amihot Test, bearing material containing copper and lead is placed in the tube containing a portion of lubricating oil containing the test additive product. To the oil is added a small amount of corrosive material such as hydrochloric acid or an alkyl halide. The lubricant and bearing material are heated in the tube to a temperature of about 162.8° C. (325° F.), and air is passed through the tube. The bearing is weighed prior to immersion in the oil and again at the end of the test after cleaning with solvent. The ability of the additive to prevent corrosion of the bearing material is reflected in the loss of weight of the bearing during immersion in the lubricating oil under test. The smaller the weight loss, the better the additive is in preventing acidic corrosive wear.

In the Motored Engine Test, an internal combustion automobile engine is driven by an electric motor. The oil pan of the engine is heated to a temperature, about 195° F., similar to the operating temperature of modern internal combustion engines. The amount of horsepower needed by the electric motor to turn the internal combustion engine by overcoming the friction between the moving parts in the engine is measured. An effective friction modifier in the lubricating oil reduces the horsepower load on the electric motor. The results of the Motored Engine Test are expressed in horsepower.

The following examples are illustrative of methods that can be used to prepare the additives of this invention. The examples should not be used to unduly limit the scope of the invention.

EXAMPLE I

To a 500 milliliter three-neck round bottom flask equipped with a reflux condenser, thermostat, water trap, thermometer, and nitrogen purge tube was charged 6.7 grams (0.046 moles) of molybdenum trioxide, 26.9 grams water, and 3.2 grams 50 percent sodium hydroxide solution. The mixture was heated to 165° F. with stirring to dissolve the molybdenum trioxide. The resulting solution of sodium molybdate was cooled to 120° F., and 2.0 grams of 96 percent sulfuric acid was added followed by 70 grams of n-heptane and 100 grams of the aminated sulfurized olefin of EXAMPLE III. The mixture was vigorously stirred at reflux for 1 hour. Water was removed by azeotropic distillation and the product purified by centrifugation and filtration through celite. Volatiles were then removed by stripping using nitrogen purge. The resulting product contained 0.7 percent nitrogen, 1.5 percent sulfur, and 2.1 percent molybdenum.

EXAMPLE II

To a 3 liter, three-neck round bottom flask equipped with a reflux condenser, thermostat, water trap, thermometer, and nitrogen purge tube was charged 67 grams (0.46 mole) of molybdenum trioxide, 269 grams of water, and 32 grams of 50 percent aqueous sodium hydroxide. The mixture was heated and stirred until the molybdenum trioxide was dissolved. 20 grams of 96 percent sulfuric acid was added followed by 600 grams of n-heptane and 1,003 grams of the aminated sulfurized olefin of EXAMPLE IV. This mixture was vigorously stirred under reflux for 4 hours. Water was removed by azeotropic distillation over a 3 hour period. The product was cooled and was allowed to stand overnight until organic residue had settled. Residual insoluble material was removed by filtration. The solvent was removed by stripping using a nitrogen purge at high temperature. The resulting product contained 0.5 percent nitrogen, about 1.7 percent sulfur, and 2.0 percent molybdenum.

EXAMPLE III

Into a 2 liter flask equipped with a reflux condenser, thermostat, water trap, thermometer, and nitrogen purge tube, was placed 554 grams of the sulfurized polyisobutylene of EXAMPLE V, 21.6 grams (0.11 mole) of tetraethylenepentamine, 40 grams (0.069 moles) of magnesium hydroxide, 20 milliliters of water and 20 milliliters of xylene. The mixture was heated and stirred to 190° C. while water and excess solvent were removed. The mixture was held at 190° C. for 45 minutes and was then cooled and diluted with heptane. The solids were removed by filtration through a coarse glass Buchner filter covered with celite. The heptane was removed by distillation under a stream of nitrogen at 180° C. The sulfurized aminated olefin product contained 0.781 percent by weight nitrogen and 1.49 percent by weight sulfur.

EXAMPLE IV

Into a 5 liter, three-neck round bottom flask having a reflux condenser, a nitrogen inlet tube, a stirrer, a heater and a water trap was charged 1192 gms of the product of Example VI, 44.50 gms (0.23 mole) tetraethylenepentamine, 75.49 gms (1.3 moles) magnesium hydroxide, 39.73 ml of water, 347.67 gms SX-5W oil and 400 ml xylene. The mixture was stirred and heated to a temperature of 160° C., under a stream of nitrogen. Water and volatile material were removed. After 5 hours at 160° C. the temperature of the reaction raised to 185° C. After 1 hour, 200 ml celite was added and the batch was cooled to 120° C. 3.7 liters of heptane was added to the reaction mixture which was then filtered through celite. Volatile material was stripped at high temperature. The product contained 1.29 wt.% sulfur and 0.529 wt% nitrogen.

EXAMPLE V

Into a 2 liter, three-neck flask equipped with a reflux condenser, thermostat, water trap, thermometer, and nitrogen purge tube was charged 600 grams (0.269 moles) of polyisobutylene and 143.12 grams (4.5 moles) of elemental sulfur. The mixture was heated to 185° C. under a nitrogen atmosphere, the nitrogen flow was stopped, and the flask was connected to a wet test meter to measure hydrogen sulfide production. The temperature of the solution was increased to about 230° C. for 7 hours. During this time, 10.05 liters of hydrogen sulfide were evolved. The sulfurized polyisobutylene was cooled, and was ready for further use.

EXAMPLE VI

Into a 2 liter resin kettle was charged 1544 gms (0.69 moles) of polyisobutylene ($\overline{M}w$ 2246) and 110.13 gms (3.4 moles) sulfur. The mixture was stirred and heated to about 200° C. and held for 24 hours. During this time about 46.7 liters of $H_2S$ was evolved indicating complete reaction. At the end of this period, the mixture was stripped of volatile material with nitrogen at 230° C. The product had a $\overline{M}w$ of 2755.

TABLE I

| TEST OIL FORMULATIONS | | | | | |
|---|---|---|---|---|---|
| | I | II | III | IV | V |
| Zinc dialkyl dithiophosphate (wt %) | 1.15 | 1.15 | 1.15 | 1.15 | 1.15 |
| Overbased magnesium sulfonate (wt %) | 1.46 | 1.46 | 1.46 | 1.46 | 1.46 |
| Calcium phenate (wt %) | 1.15 | 1.15 | 1.15 | 1.15 | 1.15 |
| Polymethacrylate VI-improver (wt %) | 7.51 | 7.51 | 7.51 | 7.51 | 7.51 |
| Silicon antifoam (wt %) | 0.10 | 0.10 | 0.10 | 0.10 | 0.10 |
| Prod. EX. I (wt %) | — | 4.1 | — | — | — |
| Prod. EX. II (wt %) | — | — | 5.8 | — | — |
| Prod. EX. III (wt %) | — | — | — | 4.1 | — |
| Prod. EX. IV (wt %) | — | — | — | — | 5.8 |
| Commercial Mannich Dispersant | 4.1 | — | — | — | — |
| Lub. Oil | Bal. | Bal. | Bal. | Bal. | Bal. |

TABLE II

BENCH TESTS OF MOLYBDENUM AMINATED SULFURIZED OLEFIN

| Test Oil | Amihot Pb (mgm) | Amihot Cu (mgm) | Air HTT (495° F.) | OTT SDT 24 | OTT SDT 48 | OTT % Vis Inc 24 | OTT % Vis Inc 48 |
|---|---|---|---|---|---|---|---|
| I | −14.2 | +0.3 | 5.0, 4.0 | 100 | 84 | 43 | 523 |
| II | −0.7 | −0.6 | 4.0 | 93 | — | 150 | TVTM* |
| III | −2.6 | −18.6 | 7.0 | 100 | 92 | 23 | 120 |
| IV | −0.6 | −0.9 | 5.0 | 100 | 100 | 4 | 34 |
| V | −2.5 | −22.1 | 6.0 | 100 | 100 | 10 | 17 |

*TVTM - Too Viscous To Measure

TABLE III

| MOTORED ENGINE TEST OIL FORMULATIONS | | | |
|---|---|---|---|
| | VI | VII | VIII |
| Polymethacrylate viscosity index improver wt % | 5.8 | 5.8 | 5.8 |
| Mannich dispersant wt % | 4.5 | — | — |
| Zinc dialkyl dithiophosphate | 1.7 | 1.7 | 1.7 |
| Overbased magnesium sulfonate wt % | 0.9 | 0.9 | 0.9 |
| Overbased calcium phenate wt % | 0.7 | 0.7 | 0.7 |
| Calcium sulfonate wt % | 0.5 | 0.5 | 0.5 |
| Product EX. I wt % | — | 4.5 | — |
| Product EX. III wt % | — | — | 4.5 |
| Lub. Oil | Bal. | Bal. | Bal. |

TABLE IV

MOTORED ENGINE TEST RESULTS WITH A MOLYBDENUM AMINATED SULFURIZED OLEFIN

| Test Oil | Friction Horsepower @ °C. (°F.) | | | |
|---|---|---|---|---|
| | 49° C. (120° F.) | 71° C. (160° F.) | 93° C. (200° F.) | 104° C. (220° F.) |
| VI | 11.74 | 10.50 | 10.05 | 10.08 |
| VII | 11.66 | 10.52 | 10.01 | 9.95 |
| VIII | 11.80 | 10.69 | 10.12 | 10.13 |

| Test Oil | Friction Horsepower @ °C. (°F.) | | | |
|---|---|---|---|---|
| | 116° C. (240° F.) | 127° C. (260° F.) | 138° C. (280° F.) | 141° C. (300° F.) |
| VI | 10.29 | 10.61 | 10.91 | 11.18 |
| VII | 10.05 | 10.25 | 10.50 | 10.82 |
| VIII | 10.32 | 10.55 | 10.82 | 11.10 |

Tables I through IV show that the molybdenum-containing aminated sulfurized olefin is about equal to a commercial dispersant in terms of dispersancy and is superior to an aminated sulfurized olefin without molybdenum and a commercial dispersant in terms of friction reduction and oxidation resistance. However, the molybdenum compound tends to be somewhat more corrosive than other commercial dispersants to the bearing material in the Amihot test. We believe that since the level of corrosion is still acceptable and can be solved by appropriate lubricant formulation, and adjustment of reactants and reaction conditions, that the corrosion is not a serious problem.

The foregoing specification is illustrative of the invention. Since many embodiments of the invention can be made, the invention resides in the claims hereinafter appended.

We claim:

1. A multifunctional lubricant additive composition providing friction reduction, oxidation resistance and dispersancy, which comprises the product of the process of reacting at a temperature of from 50°–500° C. an olefin having 10–10,000 carbon atoms with about 0.1 to about 20 moles of sulfur or a sulfur-yielding compound per mole of the olefin to form a sulfurized olefin; reacting the sulfurized olefin at a temperature of from 50°–400° C. with 0.1 to 20.0 moles of a polyamine to form an aminated sulfurized olefin and reacting the aminated sulfurized olefin at a temperature of from 50°–300° C. with about 0.1 to 10.0 moles of a molybdenum compound per mole of the olefin to form the additive composition.

2. The multifunctional lubricant additive composition of claim 1 further comprising reacting the sulfurized olefin with the polyamine in the presence of a reaction promoting amount of an alkaline earth metal.

3. A multifunctional lubricant additive composition providing friction reduction, oxidation resistance, and dispersancy, which comprises the reaction product of (a) an olefin having from 10 to 10,000 carbon atoms; (b) a polyamine having the formula $NH_2[(CH_2)_zNH]_xH$, wherein z is an integer from 2 to 12 and x is an integer from 1 to 10, and wherein z is from 2 to 6 when x is from 2 to 10; (c) sulfur or a sulfur-yielding compound and (d) a molybdenum compound; wherein the olefin is reacted with said sulfur or sulfur-yielding compound at a temperature of from 50°–500° C. to form a sulfurized olefin, the sulfurized olefin is reacted with the polyamine at a temperature of from 50°–400° C. to form an aminated sulfurized olefin, and the aminated sulfurized olefin is reacted with the molybdenum compound at a temperature of from 50°–300° C.

4. The lubricant additive composition of claim 3 wherein the amount of said molybdenum compound is about 0.1 to 10.0 moles per mole of olefin.

5. The composition of claim 3 wherein the olefin comprises a substantially amorphous or viscous polyolefin.

6. The composition of claim 5 wherein the viscous polyolefin is polyisobutylene, an ethylene-propylene copolymer, an ethylene-propylene-diene terpolymer, or mixtures thereof.

7. The composition of claim 3 wherein the polyamine comprises a polyalkylenepolyamine.

8. The composition of claim 7 wherein the polyalkylenepolyamine is ethylenediamine, diethylenetriamine, tetraethylenepentamine, triethylenetetramine, hexamethylenediamine or mixtures thereof.

9. The composition of claim 3 wherein the molybdenum compound is molybdic oxide, ammonium molybdate, molybdenum halide, or mixtures thereof.

10. The composition of claim 8 wherein the molybdenum compound comprises an aqueous solution of a molybdenum compound.

11. A lubricant comprising a major portion of a lubricating oil and about 0.01 to 10.0 wt% based on the oil of the product of claim 1 or 3.

* * * * *